(12) United States Patent
Levy

(10) Patent No.: US 7,076,437 B1
(45) Date of Patent: Jul. 11, 2006

(54) PROCESS FOR CONSUMER-DIRECTED DIAGNOSTIC AND HEALTH CARE INFORMATION

(76) Inventor: Victor Levy, 300 Jeffords St., Suite A, Clearwater, FL (US) 33756

( * ) Notice: Subject to any disclaimer, the term of this patent is extended or adjusted under 35 U.S.C. 154(b) by 692 days.

(21) Appl. No.: 09/698,787

(22) Filed: Oct. 27, 2000

Related U.S. Application Data

(60) Provisional application No. 60/162,564, filed on Oct. 29, 1999.

(51) Int. Cl.
  *G06F 17/60* (2006.01)
(52) U.S. Cl. .............................. 705/3; 705/2; 600/300; 706/21
(58) Field of Classification Search ................ 600/300, 600/301, 508, 484; 705/3, 2; 706/15, 21, 706/45, 20, 52; 434/262; 704/270
See application file for complete search history.

(56) References Cited

U.S. PATENT DOCUMENTS

| | | | | |
|---|---|---|---|---|
| 4,130,881 | A | * | 12/1978 | Haessler et al. ................ 705/3 |
| 4,513,438 | A |   | 4/1985 | Graham et al. |
| 4,699,153 | A |   | 10/1987 | Shevrin et al. |
| 4,864,140 | A |   | 9/1989 | Rogers et al. |
| 4,957,115 | A |   | 9/1990 | Selker |
| 5,077,677 | A |   | 12/1991 | Murphy et al. |
| 5,101,200 | A |   | 3/1992 | Swett |
| 5,277,188 | A |   | 1/1994 | Selker |
| 5,292,636 | A |   | 3/1994 | Kung et al. |
| 5,299,121 | A |   | 3/1994 | Brill et al. |
| 5,327,893 | A |   | 7/1994 | Savic |
| 5,363,298 | A |   | 11/1994 | Survanshi et al. |
| 5,364,759 | A |   | 11/1994 | Caskey et al. |
| 5,380,667 | A |   | 1/1995 | Schwertner |
| 5,404,292 | A | * | 4/1995 | Hendrickson ................ 600/301 |
| 5,417,971 | A |   | 5/1995 | Potter et al. |
| 5,419,331 | A |   | 5/1995 | Parker et al. |
| 5,433,216 | A |   | 7/1995 | Sugrue et al. |
| 5,434,046 | A |   | 7/1995 | Enns et al. |
| 5,441,736 | A |   | 8/1995 | Gerlach et al. |
| 5,501,229 | A |   | 3/1996 | Selker et al. |
| 5,521,072 | A |   | 5/1996 | Potter et al. |
| 5,529,907 | A |   | 6/1996 | Nierman et al. |
| 5,572,421 | A | * | 11/1996 | Altman et al. .................. 705/3 |
| 5,583,758 | A | * | 12/1996 | McIlroy et al. ................. 705/2 |
| 5,593,849 | A |   | 1/1997 | Roy |
| 5,626,140 | A | * | 5/1997 | Feldman et al. ............ 600/484 |

(Continued)

FOREIGN PATENT DOCUMENTS

GB 2328507 A * 2/1999

OTHER PUBLICATIONS

Ingram, R. Accounting Information Systems. 1998. Culverhouse School of Accountancy. University of Alabama. [Retrieved on Jun. 1, 2004]. Retrieved from the Internet. URL<http://www.cba.ua.edu/accounting/ringram/Accounting%20Information%20Systems.doc>.*

(Continued)

*Primary Examiner*—Joseph Thomas
*Assistant Examiner*—Natalie A. Pass

(57) ABSTRACT

There is disclosed a process and an apparatus for (1) facilitating patient and professional health care provider interaction and communication about a diagnosis that requires a professional decision, and (2) providing patients with a means for making their own health care decisions by empowering patients with the means for potential self diagnosis of symptoms.

1 Claim, 15 Drawing Sheets

U.S. PATENT DOCUMENTS

| | | | |
|---|---|---|---|
| 5,632,276 | A | 5/1997 | Eidelberg et al. |
| 5,649,061 | A | 7/1997 | Smyth |
| 5,671,294 | A | 9/1997 | Rogers et al. |
| 5,698,195 | A | 12/1997 | Le et al. |
| 5,716,853 | A | 2/1998 | Cuckle et al. |
| 5,718,233 | A | 2/1998 | Selker et al. |
| 5,763,168 | A | 6/1998 | Lalouel et al. |
| 5,778,345 | A * | 7/1998 | McCartney .................... 705/2 |
| 5,801,018 | A | 9/1998 | Potter et al. |
| 5,811,233 | A | 9/1998 | Bowcock et al. |
| 5,815,198 | A | 9/1998 | Vachtesevanos et al. |
| 5,868,669 | A | 2/1999 | Iliff |
| 5,911,132 | A * | 6/1999 | Sloane ......................... 705/3 |
| 5,915,240 | A | 6/1999 | Karpf |
| 6,024,699 | A | 2/2000 | Surwit et al. |
| 6,029,138 | A * | 2/2000 | Khorasani et al. ............ 705/2 |
| 6,053,866 | A * | 4/2000 | McLeod ..................... 600/300 |
| 6,076,083 | A * | 6/2000 | Baker .......................... 706/52 |
| 6,149,585 | A * | 11/2000 | Gray .......................... 600/300 |
| 6,177,940 | B1 * | 1/2001 | Bond et al. .................. 434/262 |
| 6,185,534 | B1 * | 2/2001 | Breese et al. ............... 704/270 |
| 6,206,829 | B1 * | 3/2001 | Iliff ............................ 600/300 |
| 6,267,722 | B1 * | 7/2001 | Anderson et al. ........... 600/300 |
| 6,336,108 | B1 * | 1/2002 | Thiesson et al. .............. 706/20 |
| 6,556,977 | B1 * | 4/2003 | Lapointe et al. .............. 706/15 |

OTHER PUBLICATIONS

Blinowska. A. et al., "Diagnostica-A Bayesian Decision-Aid System-Applied to Hypertension Diagnosis," 1993, [Retrieved on Aug. 16, 2005]. Retrieved from the Internet: URL: :<http://ieeexplore.ieee.org/iel5/10/5657/00216406.pdf?arnumber=216406>.*

Sonis. "How to Use and Interpret Interval Likelihood Ratios," Jun. 1999, [Retrieved on Aug. 16, 2005]. Retrieved from the Internet: URL: <http://www.stfm.org/fmhub/Fullpdf/june99/rs.pdf>.*

Blinowska, A. et al., Bayesian Statistics as Applied to Hypertension Diagnosis. IEEE Transactions on Biomedical Engineering. vol. 38, No. 7, 1991. [Retr. Aug. 16, 2005]. Retrieved from the Internet: URL: <http://ieeexplore.ieee.org/iel1/10/2725/00083571.pdf>.*

Hamilton, R. FDA Examining Computer Diagnosis. FDA Consumer magazine. Sep. 1995. [Retrieved on Aug. 16, 2005]. Retrieved from the Internet: URL: <http://www.fda.gov/fdac/features/795_compdiag.html>.*

Lemaire, J. et al., Effectiveness of Quick Medical Reference as diagnostic tool. Can. Med. Assoc.Jour. Sep. 1999. [Retr. Aug. 16, 2005]. Retr. Internet: URL: <http://epe.lac-bac.gc.ca/100/201/300/cdn_medical_association/cmaj/vol-161/issue-6/pdf/pg725.pdf>.*

Products—Iliad 4.5 page. A.D.A.M. Software website. Feb. 1998. [Retrieved on Aug. 16, 2005]. Retrieved from the Internet: URL: <http://web.archive.org/web/19980203083438/http://www.adam.com/hc_iliad.html>.*

P. Moayyedi and A.T.R. Axon, The Usefulness of the Likelihood Ratio in the in the Diagnosis of Dyspesia and Gastroesoobageal Reflex Disease, The American Journal of Gastroenterology, 1999, 3123-3125, vol. 94, No. 11.

Dudley RA, Can Hospital Selection Avoid Deaths?, Internal Medicine Alert, JAMA 2000; 283:1159-1166, pp. 67-68.

P.Pisek, Innovative Thinking for the Improvement of Medical Systems, Annals of Internal Medicine, pp. 438-444, Sep. 21, 1999, vol. 131, No. 6.

R.A. Dudley, K. Johansen, R. Brand, D. Rennie, and A. Milsiein, Selective Referral to High-Volume Hospitals, JAMA, Mar. 1, 2000, vol. 283, No. 9.

R.P. Fleet, G. Dupuis, A. Marchand, D. Burelle, and P.D. Bettman, Detecting Panic Disorder in Emergency Department Chest Pain Patients: A Validated Model to Improve Recognition, Annals of Behavioral Medicine, 1997 Spring, 19(2):124-131, Abstract only.

Ingram, Robert W., Accounting Information Systems—Notes for AC 389/489, Spring/Fall 1998, Culverhouse School of Accountancy, University of Alabama, USA.

Pozen, M.W.; D'Agostino, R.B.; Selker, H.P.; Sytkowski, P.A.; Hood, W.B., Jr.; A Predictive Instrument to Improve Coronary Care-Unit Admission Practices in Acute Ischemic Heart Disease: A Prospective Multicenter Clinical Trial, N. Engl. J. Med. 1984; 310-1273-1278.

Goldman, L.; Cook, E.F.; Brand, D.A., et al.; A Computer Protocol to Predict Myocardial Infarcation in Emergency Department Patients with Chest Pain, N. Engl. J. Med. 1988, 318; 797-803.

Selker, H.P.; Beshansky, J.R.; Griffith, J.L.; et al.; Use of the Acute Cardiac Ischemia Time-Insensitive Predictive Instrument (ACI-TIPI) to Assist with Triage of Patients with Chest Pain or Other Symptoms Suggestive of Acute Cardiac Ischemia: a Multi-Center, Controlled Clinical Trial, Ann Intern Med. 1998; 129:845-855.

Dawson-Sanders, Beth, and Trapp, Robert G., Basic & Clinical Biostatistics, 1994, pp. 1, 2, 241-242, Paramount Publishing Business and Professional Group, U.S.A.

* cited by examiner

PROCESS FOR CONSUMER-DIRECTED DIAGNOSTIC AND HEALTH CARE INFORMATION

RELATED APPLICATION

The present application claims the benefit of the filing date under 35 U.S.C. § 119(e) to provisional U.S. Patent Application Ser. No. 60/162,564 filed on Oct. 29, 1999, which is hereby incorporated by reference.

TECHNICAL FIELD OF THE INVENTION

The present invention provides a process and an apparatus for (1) facilitating patient and professional health care provider interaction and communication about a diagnosis that requires a professional decision, and (2) providing patients with a means for making their own health care decisions by empowering patients with the means for potential self diagnosis of symptoms.

BACKGROUND OF THE INVENTION

Health care Internet sites have been among the most rapidly growing Internet destinations in terms of consumer/user visits. Such sites offer medical and health care information in the form of news, medical literature or library resources on-line. Often the information is organized along disease lines to facilitate advertising directed at target audiences and to facilitate formation of "chat" or other on-line discussions or support conversations among interested users.

A patient or user of the traditional on-line health sites looking to understand or diagnose a medical situation would require the patient to explain his or her symptoms and then read through discussion of various diseases in a medical reference text (or even an on-line version) while attempting to match his or her symptoms to a disease. This process is much like shopping for items in a grocery store by looking solely at the list of ingredients on package labels and then attempting to find a desired item by locating the matching list of ingredients.

Common tools used to determine probabilities in the clinical research and disease management area have typically revolved around probabilities associated with sensitivity and specificity. Sensitivity is defined as the proportion of false negatives we should expect of people that truly have a disorder. Specificity is defined as the proportion of false positives among those without the disease.

Therefore, despite the proliferation of on-line health care information sites, there is a need to provide an on-line diagnostic system for helping to match symptoms to potential diseases or diagnoses such that a patient can obtain information for traditional sources prior to a visit to a health care professional.

SUMMARY OF THE INVENTION

The present invention provides a process for facilitating patient self-diagnosis of symptoms comprising the steps of:
(a) providing a plurality of entry points that are symptoms that the patient will indicate are present;
(b) providing a plurality of disease categories that the patient will check are related to the symptoms indicated in step a; and
(c) reporting a series of possible diagnoses and probabilities of such diagnoses.

Preferably, each diagnosis is linked to a series of warnings if a possible disease requires urgent treatment. Preferably, each diagnosis is linked to a disclaimer statement. Preferably, the process further comprises a step to provide any information of medications being taken, wherein possible side effects can be linked to the medications.

The present invention further provides an apparatus or server system for implementing a patient self-diagnosis service over a wide area network means of communication, wherein the server system comprises a central processing unit, ROM, RAM, and a data storage device, wherein the data storage device comprises one or a plurality of databases selected from the group consisting of a symptoms database, a disease category database, a medications database, a diseases database, a health insurers/systems database, a professionals database, and combinations thereof, wherein the symptoms database, the disease category database, and the diseases database must be present.

The invention further provides a process for designing an algorithm for evidence-based medicine differential diagnoses, comprising:
(a) providing a presenting symptom or group of symptoms;
(b) determining evidence-based probabilities for each diagnosis from medical literature or clinical experience sources;
(c) merging the probabilities with aggregated data into decision alternatives; and
(d) listing first and preference values as algorithm branch-point choices.

In a further embodiment, the method for determining a diagnosis includes:
(a) providing symptomatic information;
(b) analyzing the symptomatic information using a likelihood ratio algorithm; and
(c) determining a diagnosis based on a resulting calculation of the likelihood ratio algorithm.

One advantage of the present method is the ability to construct greater than "2×2" tables. The method may be used in all patient populations regardless of prevalence. thereby freeing the for the evaluation of more than two alternatives or outcome possibilities and/or more than two variables or levels or categories of test results and/or symptoms.

Another advantage is the ability to link results of different, independent tests in succession by the multiplication of individual likelihood ratios.

DETAILED DESCRIPTION OF THE INVENTION

As will be made clear below, the general availability of personal computers and of the Internet and the advent of the present invention make possible mechanisms to enable and encourage influential consumer-directed transactions of the kinds described above and to increase the efficiencies of health care professionals' education activities and of manufacturers' marketing activities.

Definitions

Consumers shall mean to individual consumers or potential consumers of health care products and services, also to the responsible guardians of minors or of legally incompetent individuals, and also to the owners of animals receiving or potentially receiving veterinary care.

Professionals shall mean all health care professionals who have prescriptive authority (such as physicians, nurse practitioners, physicians' assistants, dentists, and veterinarians) or have influence (such as nurses, therapists, pharmacists, and chiropractors) in the choice and prescription of products.

Health Care Systems shall mean the administrative or business units in the vast network of managed care and insurance reimbursement systems and includes, for example, health maintenance organizations (HMOs), managed care providers, health insurance programs, pharmacy benefit managers, and other provider or payor based programs that can control, in any way, the dispensing of health care services.

Doctor shall mean any health care professional with prescriptive authority or influence for health care products or services.

Governmental Regulators and Governmental Administrators refer to those individuals who either regulate or approve (or deny) the marketing of products by manufacturers or services (e.g., Food and Drug Administration), or those State (Insurance Commissioner) or Federal (Health and Human Services) agencies that regulate which products or services must be provided or reimbursed in health care systems (e.g., HMOs) or federal health benefit systems (e.g., Medicare and Medicaid).

Network Architecture

Figure 1:
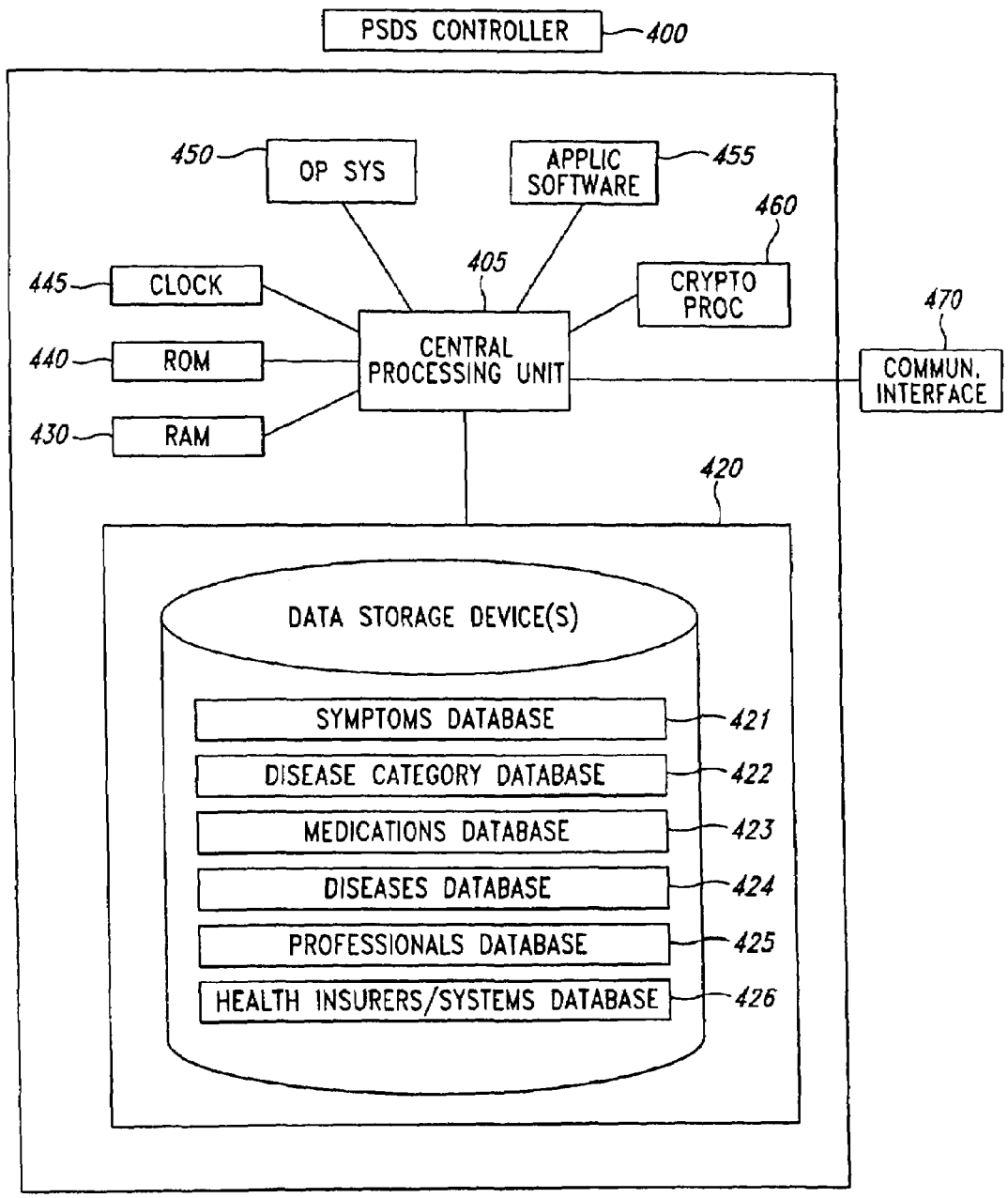
FIG. 1 illustrates a PSDS Controller in a block diagram format showing an embodiment of the computer controller of the PSDS interface.
Figure 2A:
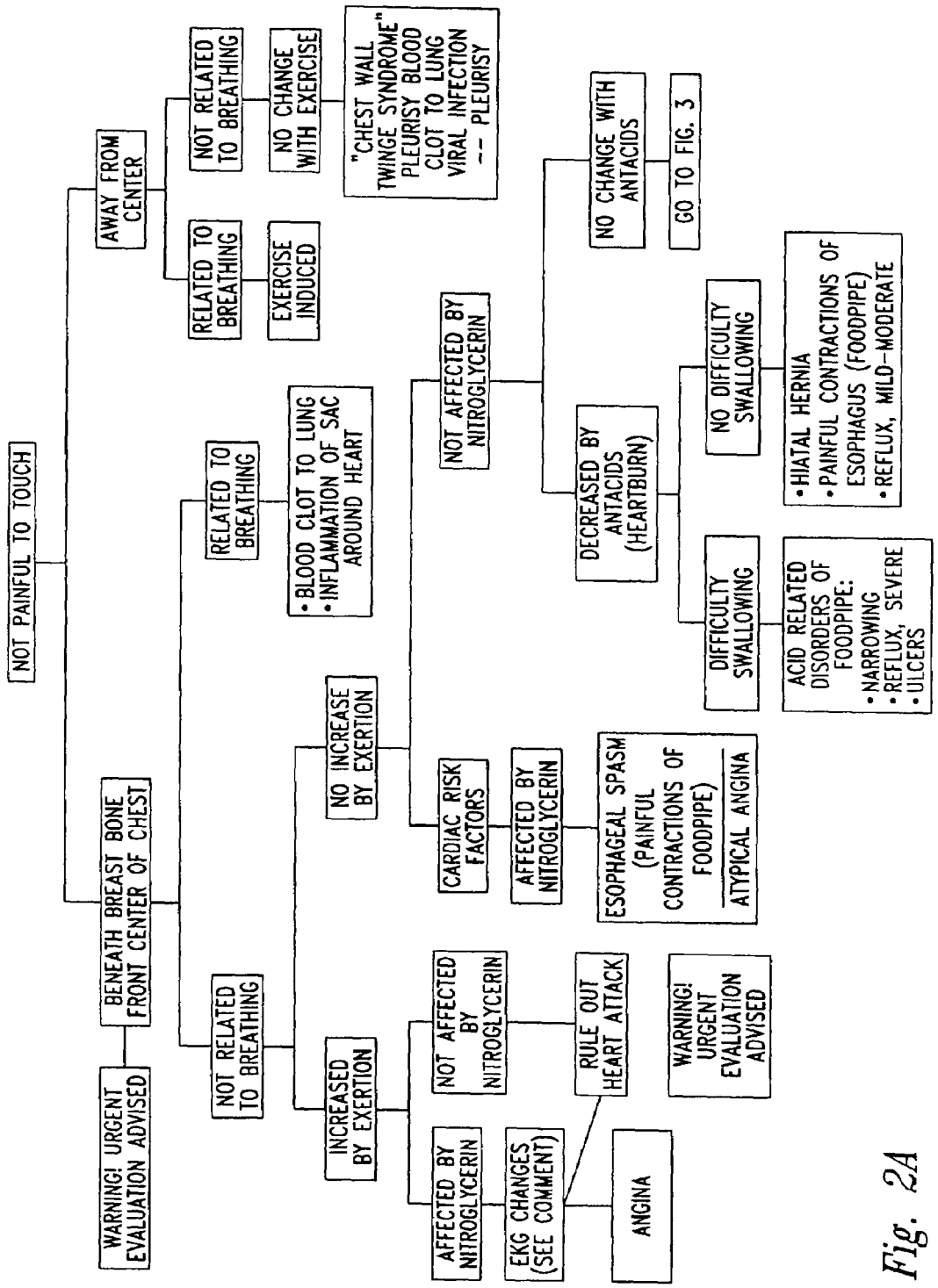
FIG. 2 shows a first page of a decision tree that begins with the symptom of chest pain. This tree goes down the routes of tenderness with palpation and no tenderness with palpation. Possible diagnoses are listed at the bottom of each tree or a link for additional information.
Figure 2B:
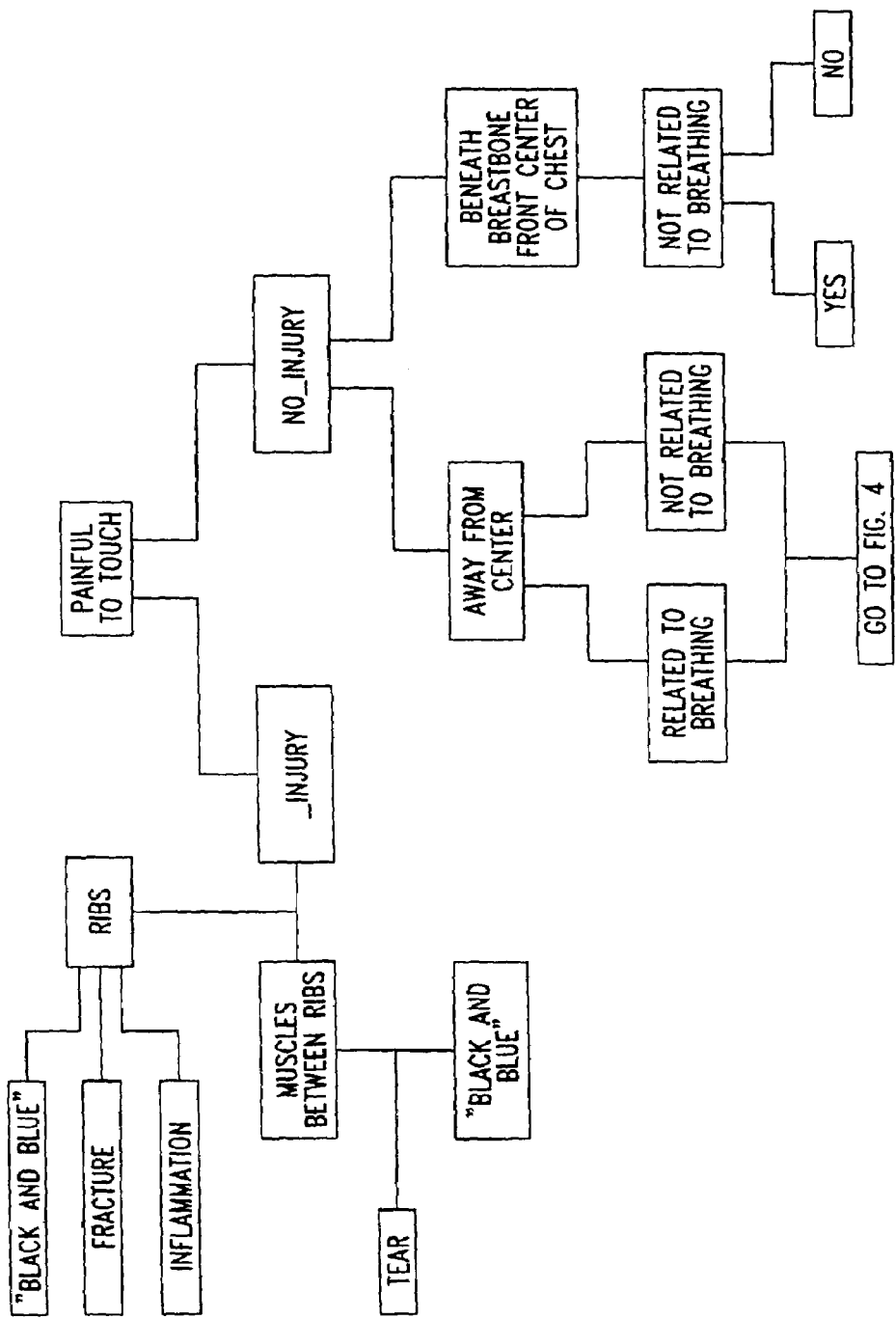
Figure 3:
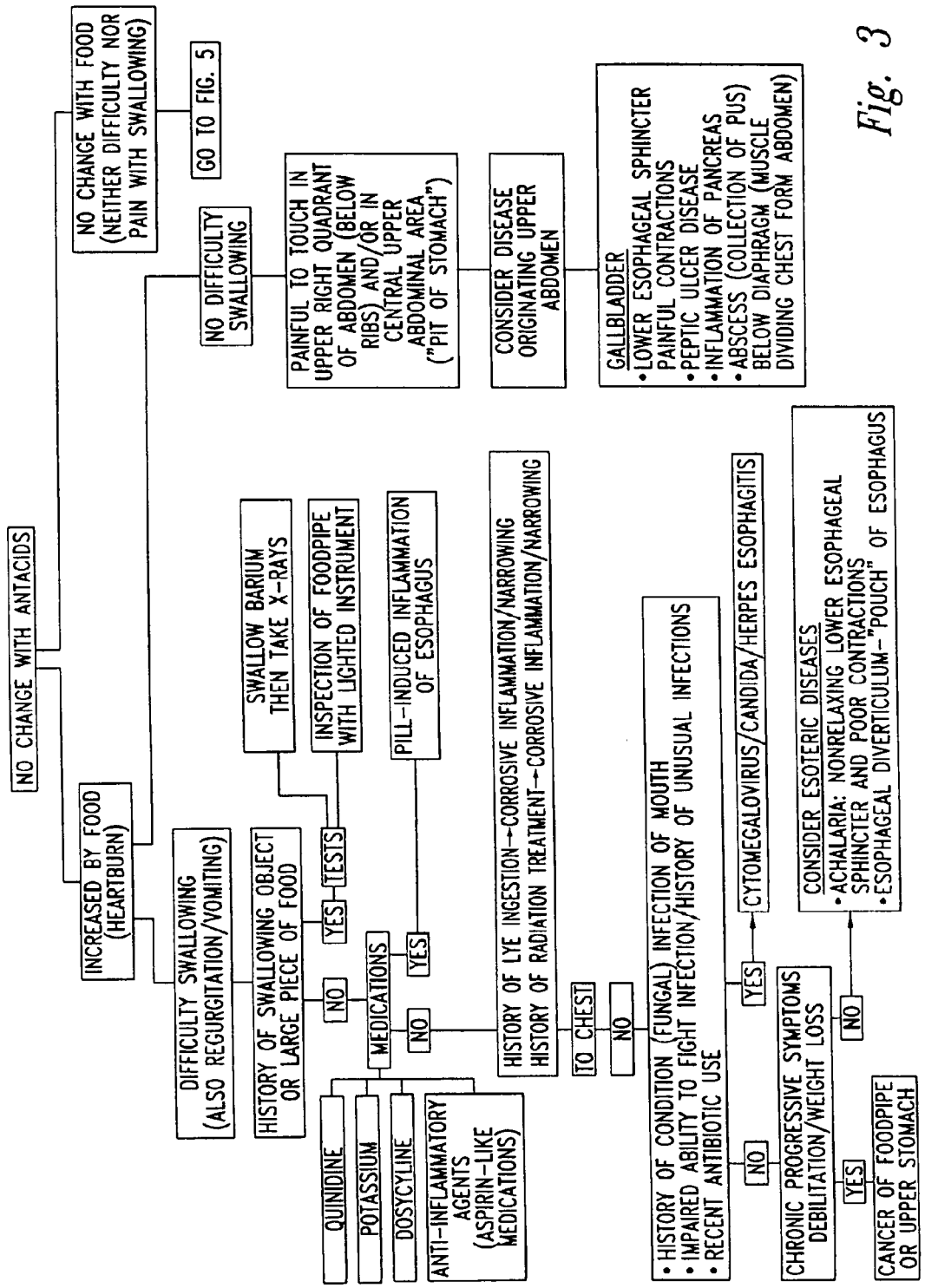
FIG. 3 utilizes additional information as to whether or not a change in the symptoms happened with administration of an antacid. The medication database is factored into the decision tree at the left.
Figure 4:
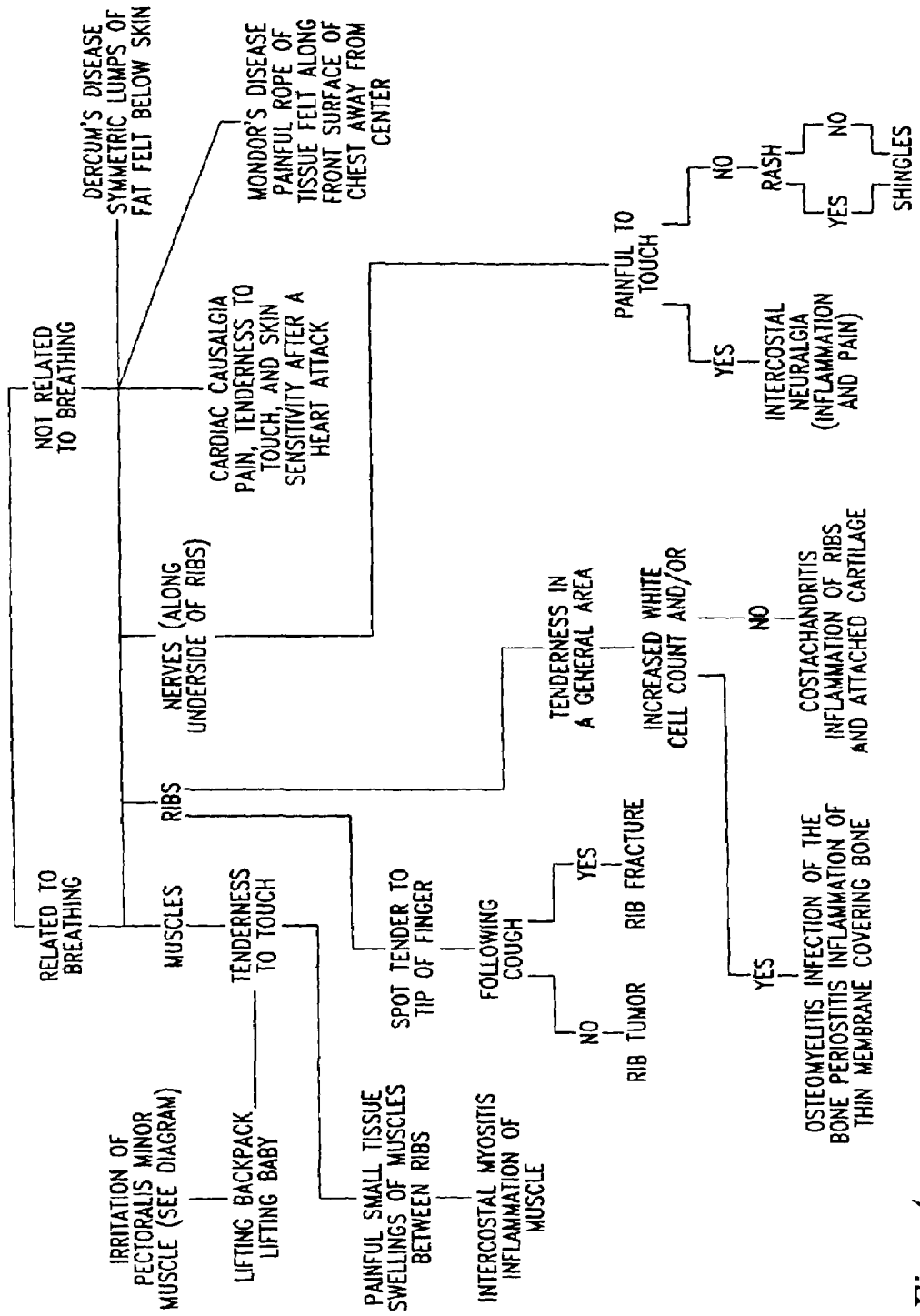
FIG. 4 shows a further continuation of the decision tree of FIG. 3 with additional possible diagnoses listed across the bottom.
Figure 5:
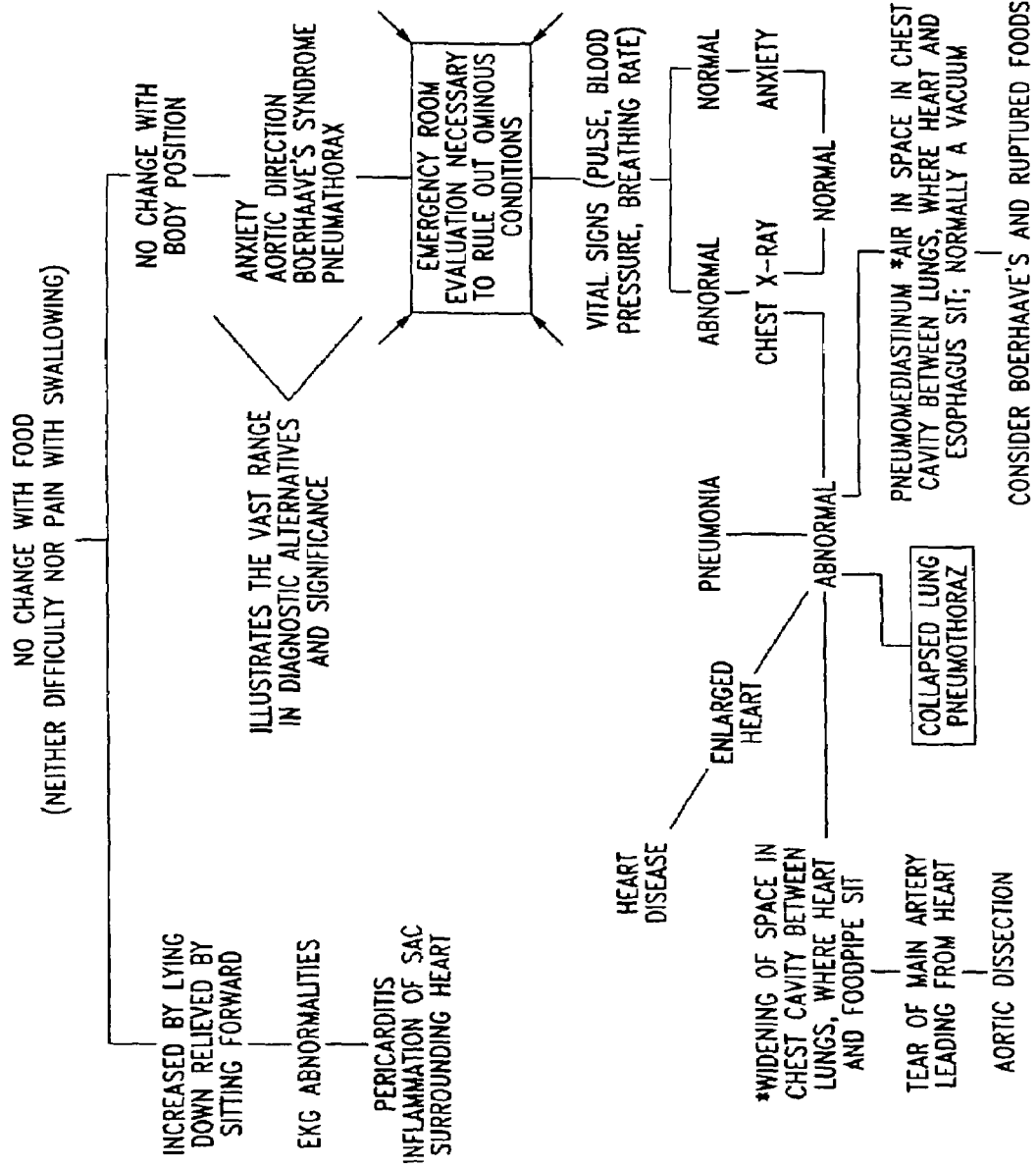
FIG. 5 shows a continuation of the decision tree of FIG. 4.

The components of a preferred embodiment of the present invention are illustrated in FIG. 1. A standard personal computer or computer workstation with adequate processing power and memory may be used as PSDS Controller 400. In one embodiment it operates as a web server, receiving and responding to consumer requests for access to PSDS services. PSDS Controller 400 must be capable of rapidly performing database queries as well as handling input and output needs. A Sun Microsystems 300 MHz UltraSparc II processor may be used for CPU 405. A similar processor such as a 500 MHz Compaq Alpha 21164 or 450 MHz Intel Inc. Pentium II may also be used.

Cryptography processor 460 may be configured as part of CPU 405 or utilize a dedicated processor such as a Semaphore Communications Roadrunner 284 or VLSI Technology 6868. Cryptography processor 460 is used to encrypt potentially sensitive data during transfer between the PSDS Controller 400 and a consumer's computer.

Operating system 450 provides application software 455 with interface to CPU 405, data storage devices 420, RAM 430, ROM 440, clock 445, and communications interface 470. In one embodiment, operating system 450 may be a commonly available system such as Sun Microsystems' Solaris 7. Possible alternatives include Microsoft Corporation's Windows NT Server or Compaq's Digital UNIX.

Application software 455 consists of software needed to carry out functions of central controller 400. This software may include database management software, such as Oracle Corporation's Oracle8, web server software such as Netscape Communications Corporation's Enterprise Server, and custom-developed applications needed to handle consumer requests 100 for access to CDPI services.

Data storage device(s) 420 consist of storage media such as hard disk magnetic storage, magnetic tape, or CD-ROM drives. Data storage device(s) 420 consist of databases used in the processing of transactions in the present invention. In the preferred embodiment, these databases consist of a Systems Database 421, a Disease Category Database 422, a Medications Database 423, a Diseases Database 424, a Professionals Database 425, and a Health Insurers/Systems Database 426. Software such as the aforementioned Oracle8 may be used to create and manage these databases. Data storage device also contains operating system 450 and application software 455.

The Symptoms Database 421 contains a series of decision trees that start with a symptom, such as chest pain or a stomach ache or lower back pain and lead to possible diseases underlying the manifestation of the symptom. The fields of each decision tree, starting with a symptom or a cluster of symptoms, have inputs for likely disease category from the disease category database 422 (having overlapping fields for symptoms) and from the medication database 423 having overlapping fields for symptoms resulting from medication effects and side effects. This information in the symptom database can be entered by data transfer, or keyed entry by PSDS personnel, or by other systems for data input.

Disease Category Database 422 contains information about the diseases and accompanying symptoms but grouped by organ or body system categories, such as renal or gastrointestinal or cardiac related to the organ or system having a potential disease. It contains information fields such as symptoms, diseases and probabilities of outcomes. This enables updating of diagnoses related to symptoms with experience and with new medical information. This information is automatically stored by application software 455.

Medications Database 423 contains data on each prescription and non-prescription medication and sorted by dosage, routes of administration, drug indications and drug side effects, wherein the drug indications and drug side effects fields are listed according to symptom terminology. This information is automatically stored by application software 455 whenever a transaction takes place.

Diseases Database 424 contains data on each disease, its probability of occurrence, severity and symptoms associated with each disease. The Diseases Database will also contain links to disease-specific websites to allow one to obtain more information.

Professionals Database 425 contains data on all professionals with whom the PSDS has had or has been directed to have contact. It contains fields such as a unique key, name, address, phone number, e-mail address, practice location, specialty type, disease states and products specified by consumers to be of interest, "cookies" placed in the professionals' computer memories by PSDS Controller 400, etc.

Health Insurers/Systems Database 426 contains data on which health insurance companies cover (provide reimbursement or payment for) which products and services. It contains fields such as a unique key, insurer name, geographic areas, plan and policy types, covered products, disease states indicating covered use, professionals participating in the plan, etc. Related to health care systems, similar information fields are filled and maintained, including formulary inclusion/exclusion information, criteria, text of available policies/procedures, etc. This information may be entered by PSDS personnel, manufacturers' personnel, or electronic transfer from external data sources. It may include consumer-entered reports of experiences with insurers and health care systems.

Communications Interface 470 is the connection through which the central controller 400 communicates with the Internet. In a preferred embodiment, Communications Interface 470 is connected using high-speed data lines such as T1 or T3 lines to the Internet. In this preferred embodiment, communications will be handled by commercial web server hardware and software, assisted by custom software. Communications Interface 470 may also be configured other ways such as an interactive telephone response system or electronic mail automated messaging system.

Although the above embodiment describes a single computer, the Central System Controller 400 functions may be distributed across more than one computer system. In another embodiment, the central controller might consist of separate systems each handling a specific task, such as a database system and a web server system. Multiple systems may also be used in each role to provide redundancy in case of connectivity or hardware failures.

Evidence-Based Medicine

The inventive Internet process utilizes an evidence-based medicine approach as useful to health care providers in helping a patient make a diagnostic or a therapeutic decision. By contrast, "traditional medicine" comprises four assumptions. The first is that individual clinical experiences provide the foundation for diagnosis, treatment and prognosis, with the measure of authority being proportional to the weight of individual experience. The second assumption is that pathophysiology provides a foundation for clinical practice. The third assumption is that traditional medical training and common sense are sufficient to enable a physician to evaluate new tests and treatments. The fourth assumption is that clinical experience and expertise in a given subject area are sufficient foundation to enable a physician to develop clinical practice guidelines.

Evidence-based medicine, by contrast has three assumptions. The first is that when possible, clinicians use information derived from systematic, reproducible and unbiased studies to increase their confidence in the true prognosis, efficacy of therapy and usefulness of diagnostic tests. The second is that an understanding of pathophysiology is necessary but insufficient for the practice of clinical medicine. The third is that an understanding of certain rules of evidence is necessary to evaluate and apply medical literature effectively. The framework of evidence-based medicine has been used for decision-making techniques to support managed care. The decision-making is rigorous in construction and supported by statistical models. The principles of evidence-based medicine are preferably employed in the algorithms used to design the decision-tree databases described herein.

The present algorithms provided herein are formed based upon statistical probabilities for diagnoses. For example, for a given medical problem or symptom, one generates a differential diagnosis. Before any test is performed, each diagnosis in a differential is a probability of being present, also called a pretest probability. Once a test is performed, the probabilities may change for a particular diagnosis to be present. The process of refining probability helps the health care provider to determine the likelihood of each given disease process in a differential, to assist in making a diagnosis.

The inventive process uses disease and symptom-based algorithms made up using the vast body of medical literature in the form of sensitivities and specificities as values in relation to systems, physical findings, test results and therapies. Using mathematical tools employed by statisticians (e.g., statistical analysis), sensitivities and specificity's can be converted to likelihood ratios (LR), odds and ultimately probabilities. Thus, a chain of "likelihood ratios" can be multiplied to produce a product, wherein the product represents accumulated probabilities. The algorithms come in two fashions, a branchtree and a table. Table algorithms list alternative diagnoses for a given symptom in order of likelihood, with assigned probabilities. Branchtree algorithms are followed through and ultimately lead to a discrete diagnosis, so long as branchpoint choices are made. If a user is unable to make a branchpoint choice, a user will have to proceed down both sides of a branchpoint to result in numerous and disparate alternatives, especially if the point of indecision was relatively early on the branchtree. Branchtree algorithms work better in a perfect world having clear-cut symptom identification and association. Branchtree algorithms establish likelihood of different diagnoses based upon answers to multiple questions along an algorithm. The questions asked are clinically relevant pieces of data that are related to the presence or absence of disease in the algorithm. Relative probabilities can be constructed by analyzing the medical literature to extract data that leads to probability of a specific disease being present in view of certain symptoms and associated exam findings and test results.

In view of the inventive process being Internet-based and that such inventive algorithms may be followed before a health care professional may be consulted, the Internet site will need to contain disclaimers that such an inventive algorithm is not meant to replace traditional health care delivery or serve as a basis for self-treatment absent a health care provider's recommendation.

Algorithms

The algorithms used according to the inventive process are based upon an initial listing of a symptom or symptoms. According to the schematic shown in FIG. 6, the symptom or symptoms lead to a choice of disease or categories of disease. A disease that can be provided at the ending branch of a branchtree form of algorithm will contain links to expanded data bases for more detailed information, including links to specific disease-oriented web sites to obtain more detailed information and even participate in support groups. Categories of diseases requires a further determination and more likely further testing that will require a health care provider intervention. Thus, branchpoints will often end in links to systems, such as authorization for insurance reimbursement for procedures, possible triage for urgent situations, health insurance questions, cost analyses to persuading third party payors of the economic benefits of further diagnosis and early treatment, medication alternatives and centers of excellence that specialize in certain categories of diseases. Each leads to treatment alternatives, once a disease has been identified.

The algorithms herein utilize likelihood ratios. A likelihood ratio is a clinically relevant method of reporting accuracy, and calculating the probability of having a disease after a positive or negative test. A likelihood ratio expresses results in terms of the probability of a patient having a disease. The likelihood ratio takes into account prevalence in the population of the disease and therefore the resulting ratio does not vary with variance in prevalence in the population. Likelihood ratios express results in terms of odds. The odds are the probability of an event occurring divided by the probability that it will not occur. The odds are similar to the probability when the event is rare but as the event becomes more common it is necessary to switch back and forth between probabilities and odds as shown in the following equations:

Odds=probability/(1−probability)

Probability=odds/(1+odds)

The likelihood ratio can be derived from sensitivity and specificity according to the following formulas:

Likelihood ratio for a positive test result (LR+)=sensitivity/1−specificity

Likelihood ratio for negative test result (LR−)=1−sensitivity/specificity

The odds of the disease being present after the test can then be derived from the following equation:

Post-test odds=pre-test odds×LR

Likelihood ratios can be used to determine the relationship of a variable, which is something measurable, to an outcome. For example, one variable useful in determining the presence or absence of a disease state is the usefulness of a screening test. For example, likelihood ratios can be used in determining the usefulness of *Helicobacter pylori* (H. pulori) serologies in the determination of the absence or presence of peptic ulcer disease. In a further example, one variable useful in determining the length of a hospital stay is signs or symptoms as indicators of the extent or severity of the disease. For example, the percent oxygen saturation in hospitalized Chronic Obstructive Pulmonary Disease (COPD).

that may impact on the outcome are chosen such as test result possibilities or symptom parameters. Categories within each criterion are known as criterion values.

B. Available Templates

The following table shows the criterion or variable as either a positive or negative test result. The outcome is either a positive or negative outcome, such as the presence or absence of a disease state. The following "2×2 table" shows two possible alternatives in the rows which are then multipliable by the two possible criterion and/or variables in the columns. The results determine the sensitivity and specificity for each of the two criterion values for each of the two alternatives. A classic "2×2 table" used to develop likelihood ratios is as follows:

TABLE 2

| Outcome | positive test | Negative test |
|---|---|---|
| Positive alternative | a | c |
| Negative alternative | b | d |

The following formulas are used to determine sensitivity/specificity for each of two criterion values for each of two alternatives:

| | |
|---|---|
| Sensitivity = | a/a + c |
| Specificity = | d/b + d |
| Likelihood ratios are | Then determined as follows: |
| LR(positive) = | likelihood of a positive test in patient with alternative ÷ |
| | likelihood of a positive test in patient without alternative |
| LR(positive) = | (a/a + c) ÷ (b/b + d) |
| or otherwise stated as: | |
| LR(positive) = | sensitivity/1 − specificity |
| LR(negative) = | likelihood of a negative test in patients with alternative ÷ |
| | likelihood of a negative test in patients without alternative |

$$LR(negative) = (c/a + c) \div (d/b + d) = \frac{1 - \text{sensitivity}}{\text{specificity}}$$

TABLE 1

| Variable (also referred to as Criterion) | Outcome | Example |
|---|---|---|
| 1. Symptom association | DDx of a symptom | Whether n/v in setting of chest pain suggesting a cardiac or GI etiology (algorithms) |
| 2. Usefulness of a screening test | Disease | *H. pylori* serologies in peptic ulcer disease |
| 3. Sign or symptoms as indicator of extent and/or severity of disease | Hospital length of stay | Percent oxygen saturation in hospitalized COPD patients |
| 4. Test result | Disposition | Leukocytosis in diverticulitis patients to determine in-patient vs. out-patient management |

I. Developing Likelihood Ratios for Disease Management

A. Building a Custom Algorithm Using a "Template"

Figure 11:
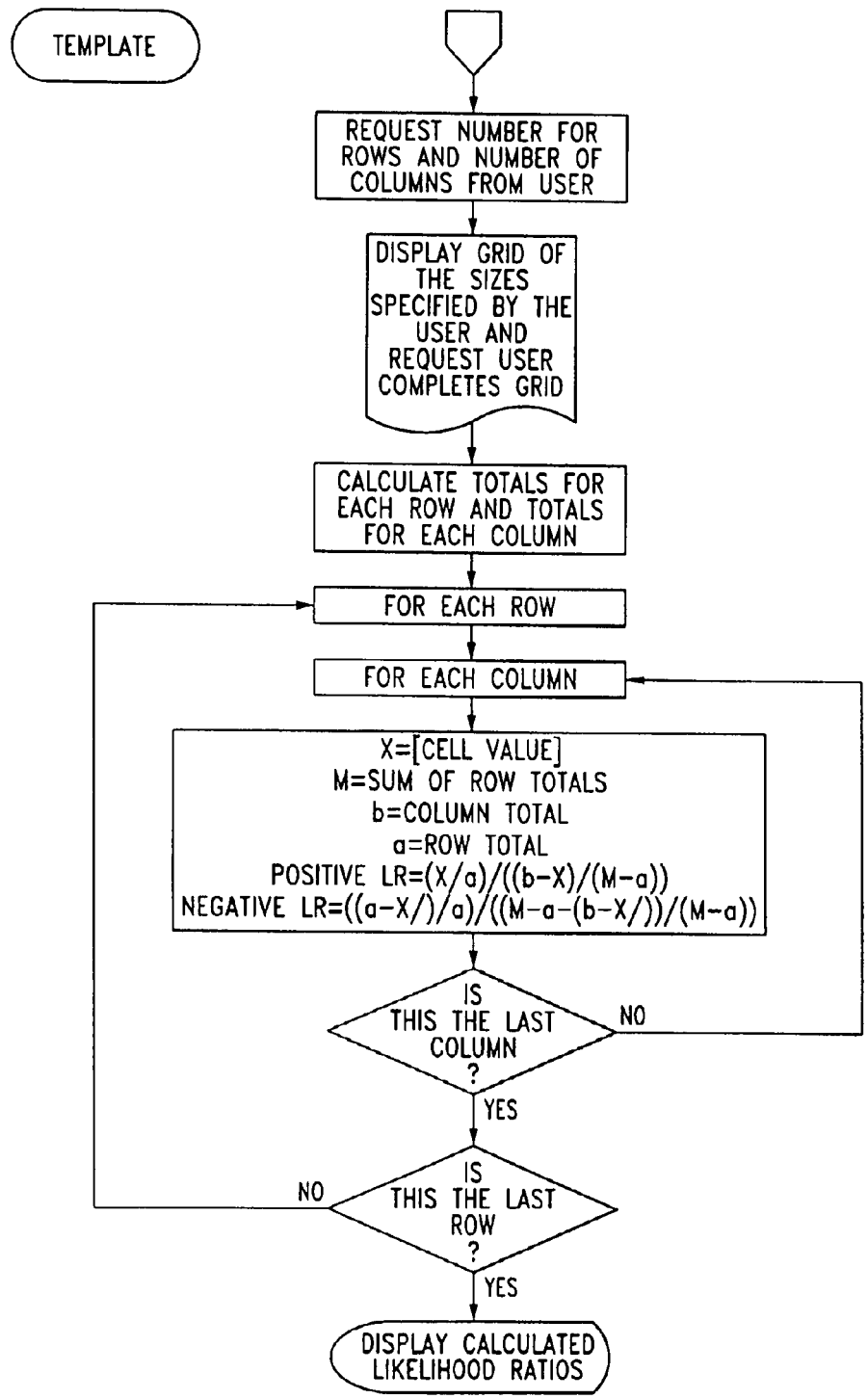
FIG. 11 shows a flow chart of the heuristics underlying a web page of a template for determining a likelihood ratio of the present invention.
Figure 12:
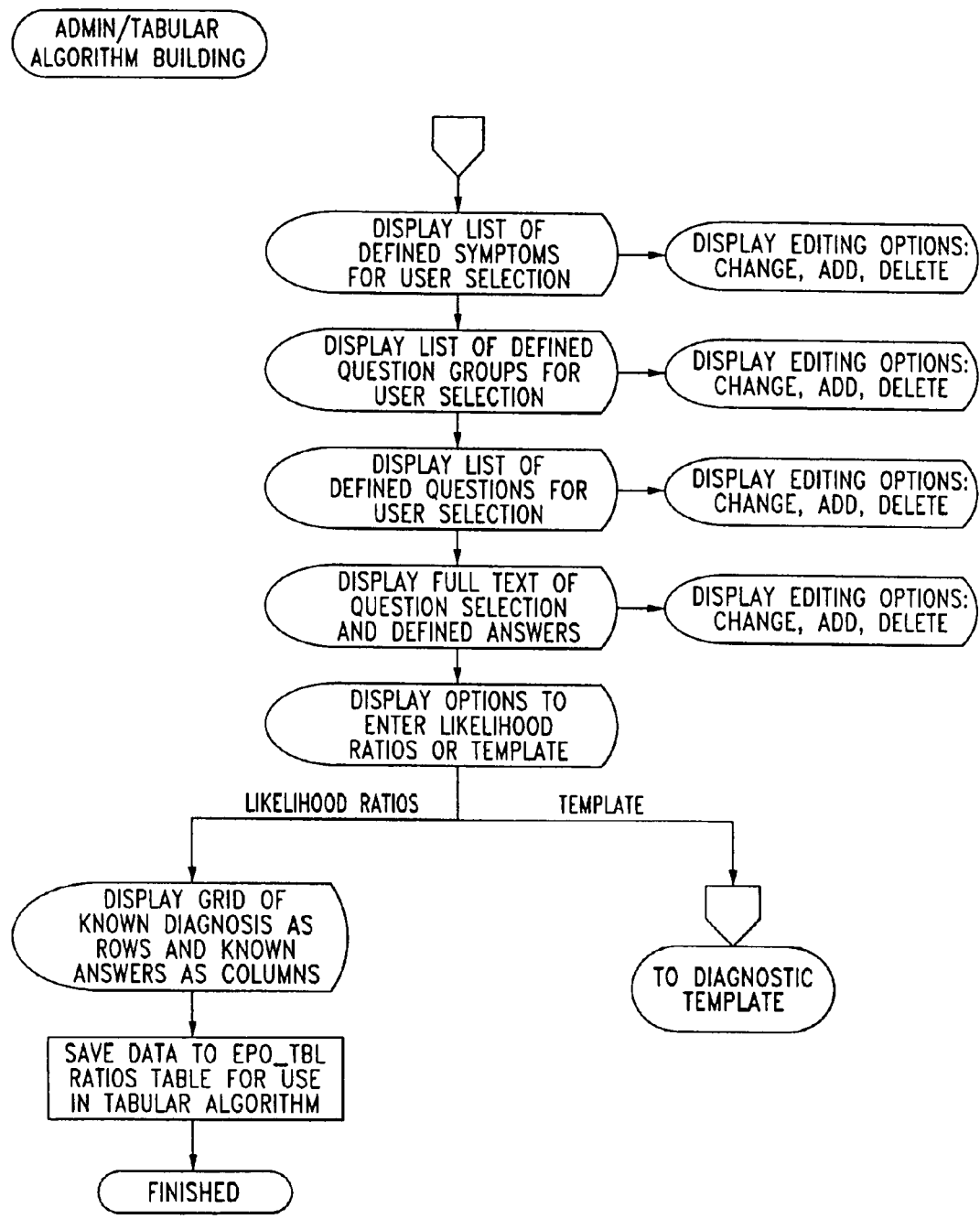
FIG. 12 shows a flow chart of administrative/tabular algorithm building.
Figure 13:
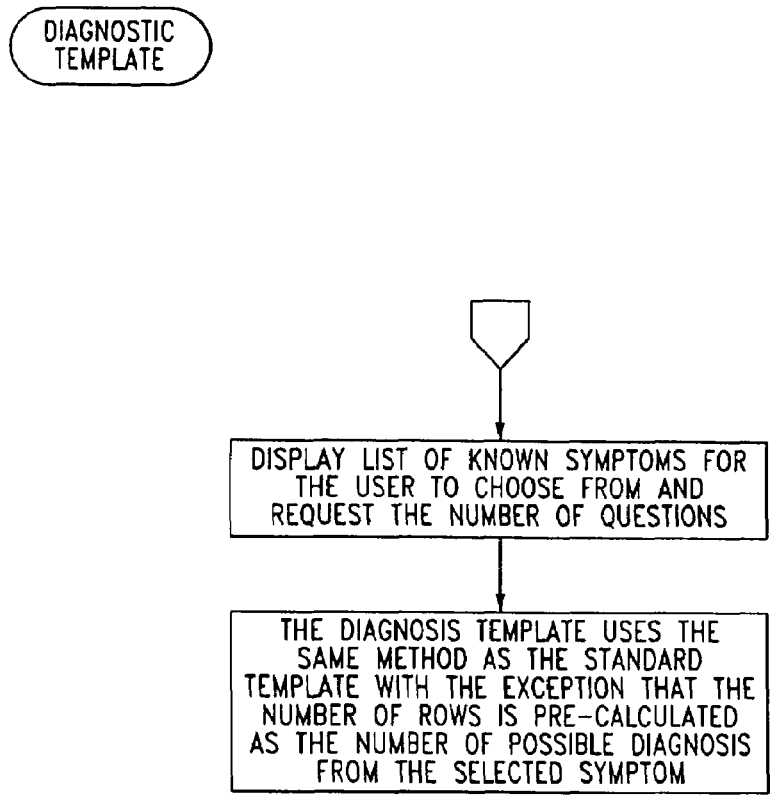
FIG. 13 shows a flow chart of the diagnostic template.
Figure 14:
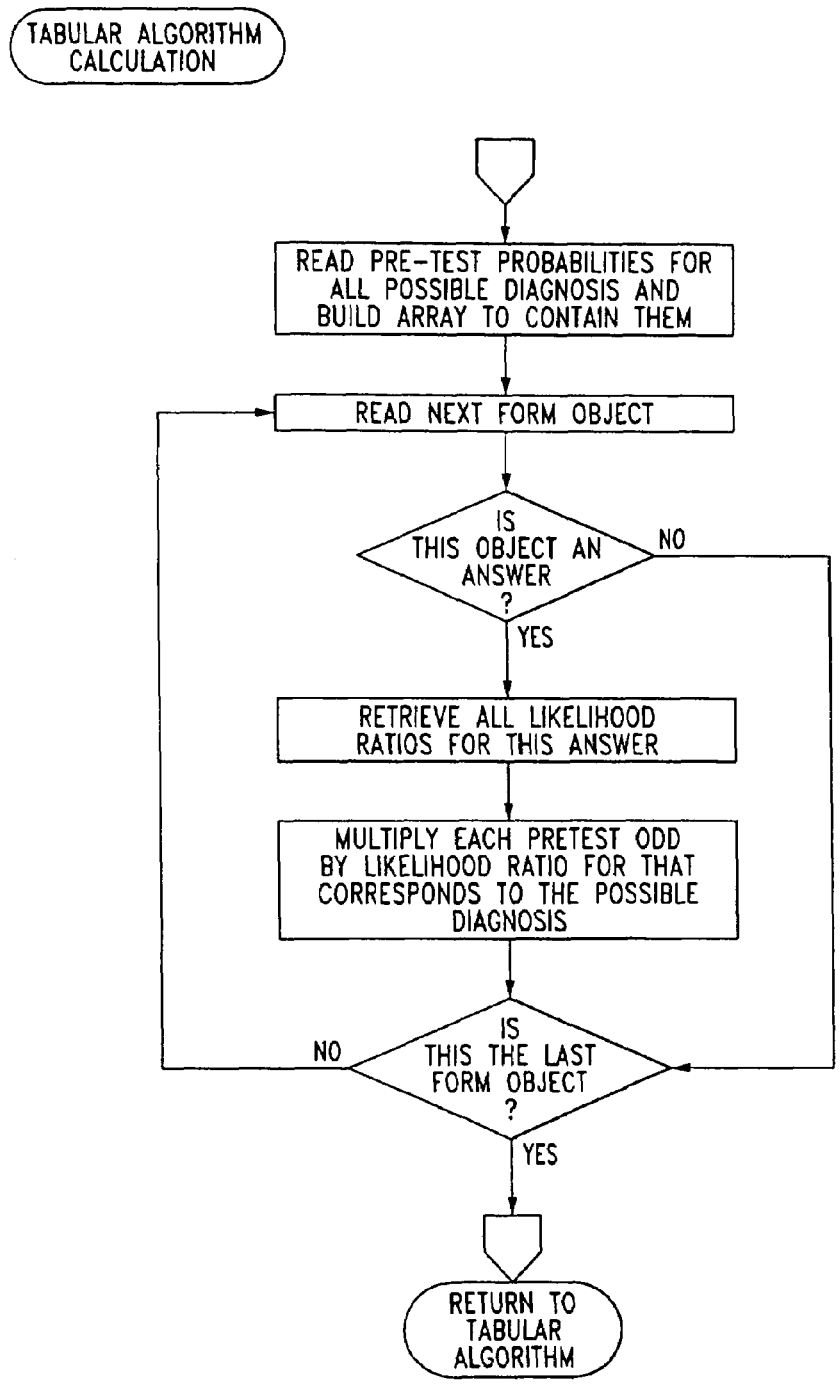
FIG. 14 shows a flow chart of the heuristics of tabular algorithm calculation.

The heuristics involved in formulating a custom template accessible to a user on a website is shown in FIG. 11. From the template, the outcome "to be improved" is chosen, and is categorized into different alternatives (choices). The outcomes are "factual statistical events" that are documented, such as a diagnosis, hospital length of stay, inpatient versus outpatient workup, etc. Criteria, also known as variables, C. Beyond the simple "2×2 table" situation having two possible variables and/or criteria are situations wherein there are a plurality of possible criteria and/or variables for a possible outcome. The following table represents a situation where there are more than two variables or criterion; such as variables beyond a positive or negative test, and the determination of likelihood ratios from the tables:

TABLE 3

| | Criterion/Variables | | | | |
|---|---|---|---|---|---|
| | 1 | 2 | 3 | 4 | Totals |
| Alternative A | | Y | | | Z |
| Alternative B | | X | | | α |

The likelihood and ratios are determined as follows:

$$LR+X = (X/\alpha) \div (y/z)$$

$$LR-X = (\alpha-X/\alpha) \div (Z-Y/Z)$$

In a further scenario, situations occur where there are a plurality of both criteria and/or variables and a more than two possible outcomes. The following table represent a situation where there are both greater than two criterion and/or variables and/or greater than two possible outcomes and/or alternatives:

TABLE 4

| | Criterion Values | | | | |
|---|---|---|---|---|---|
| | 1 | 2 | 3 | 4 | Totals |
| Outcome Alternatives | | | | | |
| A | | | | | |
| B | | X | | | α |
| C | | | | | |
| D | | | | | |
| Totals | | β | | | μ |

The likelihood ratios are determined by the following equations:

$$LR+X = (X/\alpha) \div (\beta-X/\mu-\alpha)$$

$$LR-X = (\alpha-X/\alpha) \div (\mu-\alpha)-(\beta-X)/\mu-\alpha)$$

Likelihood ratios (preference value) are computed for each criterion value. Then certain likelihood ratios of greatest significance are chosen which can be placed in succession. The likelihood ratios highest in value (positive or negative) are linked. This will alter most pretest probabilities, resulting in the greatest impact on outcome. Those LRs then determine which criteria and criterion values should be included into a custom algorithm. The following ratios apply:

series of positive LRs to confirm association series of negative LRs to confirm disassociation The pretest probabilities of each alternative are determined by dividing the number within an alternative of an outcome by the total number within an outcome. The pretest odds of each alternative are computed by the following relationship:

$$odds = p/1-p$$

The pretest odds by chosen LRs are multiplied to determine the post test odds of each alternative. The post test probabilities are determined by the following relationship:

$$post\ test\ probabilities = odds/1+odds$$

If probability observed (actual) varies from "acceptable level" of probability expected (calculated previously from database), there is then a discrepancy of "Observed vs Expected" that requires clarification and may represent opportunity for disease management. The process of disease management includes "breaking down" the case(s) under review to evaluate which specific factors (LRs) are outside an acceptable range and therefore responsible for the discrepancy. Such a process can be utilized by both integrated delivery network (IDN) and payors to assess interpractitioner variability, patient demographics, hospital specific determinants, and consultation patterns, thereby influencing outcomes.

Analysis of significant data by payors will be necessary over the next several years to reach consensus. The method of the present invention facilitates the collating, interpreting and communicating of such data. An example procedure is chosen for evaluation:

TABLE 5

| | Volume of cases at Hospitals per year: | | | | | | |
|---|---|---|---|---|---|---|---|
| | <50 | 51–100 | 101–150 | 151–200 | 201–250 | >250 | Totals |
| Survival <30 days | high | — Likelihood ratios decrease → | | | | low | Z |
| | X | B | C | D | E | F | |
| Survival >30 days | G | H | I | I | K | L | α |
| | low | Likelihood ratios increases → | | | | high | |

The following formulas are used to calculate likelihood ratios:

LR (X) = number of patients in hospitals <50 cases who died/total deaths÷number of patients in hospitals<50 cases who survived/total survivors $$LR\ (X) = X/Z/G/\alpha$$

The calculations follow the calculations discussed above in the section "likelihood rations: Building a custom algorithm using a template." Note that the table above is an adaptation of Table 2.

As the data becomes available, payors will develop alliances with certain IDNs.

II. The Analysis of Patient Selection for Cardiac Catheterization

The process of the present invention can be used to streamline the quality assurance process by an integrated deliver network (IDN) or payor.

A. Interpractionioner Variability

Understanding that patients require referral for cardiac catheterization, usually by an internist/family practitioner to a cardiologist, and then either self-referral or to an invasive cardiologist, the role of Interpractionioner variability requires evaluation.

TABLE 6

Physicians evaluating chest pain in office setting

|  | Physician 1 | | Physician 2 | | Physician 3 | | |
|---|---|---|---|---|---|---|---|
| Patients by age | <40 y | >40 y | <40 y | >40 y | <40 y | >40 y | Totals |
| OUTCOME | | | | | | | |
| Cardiac Cath. Significant disease | | | | | | | |
| Cardiac Cath. Insignificant Disease | X | B | C | D | E | F | α |
| No Cardiac Cath. | | | | | | | |
| TOTALS | β | | K | | | | μ |

An IDN with a risk contract or a payor would attempt to limit catheterizations by optimizing clinical approaches and by utilizing less expensive, less risky, non-invasive testing. The likelihood ratios dependent on the physician as the variable are based on the following:

LR(x)=LR of Physician 1's patients <40 years presenting with chest pain ultimately having a cardiac catheterization showing insignificant coronary disease.

$$=x/\alpha/\beta-x/\mu-\alpha$$

LR(x)=LR Physician 2's patients <40 years presenting with chest pain ultimately having a cardiac catheterization showing insignificant coronary disease.

$$=C/\alpha/K-C/\mu-\alpha$$

B. Assessment of Additional Factors

One can assess the value of other criteria in determining why the patient is sent for cardiac catherterization by constructing similar tables and calculating their likelihood rates. Those similar tables may include the variables of result of radionuclide cardiac scanning, stratified, continued symptoms despite maximal medical therapy, utilization of resources such as recurrent ER visits and/or hospitalizations, and/or insistence by patient or family on having the cardiac catheterization performed. These factors may be evaluated independently. Outliers and major determinants such as education/behavior modification of patients, education/behavior modification of physicians, and policy/guidelines institution, will be immediately identifiable and can be acted on.

C. Integration of Decision-Making Process

All independent criteria can now be joined in succession to determine the "collective" contribution to the overall decision to or not to catheterize.

D. Additional Non Medical Applications for Likelihood Ratios

Figure 7:
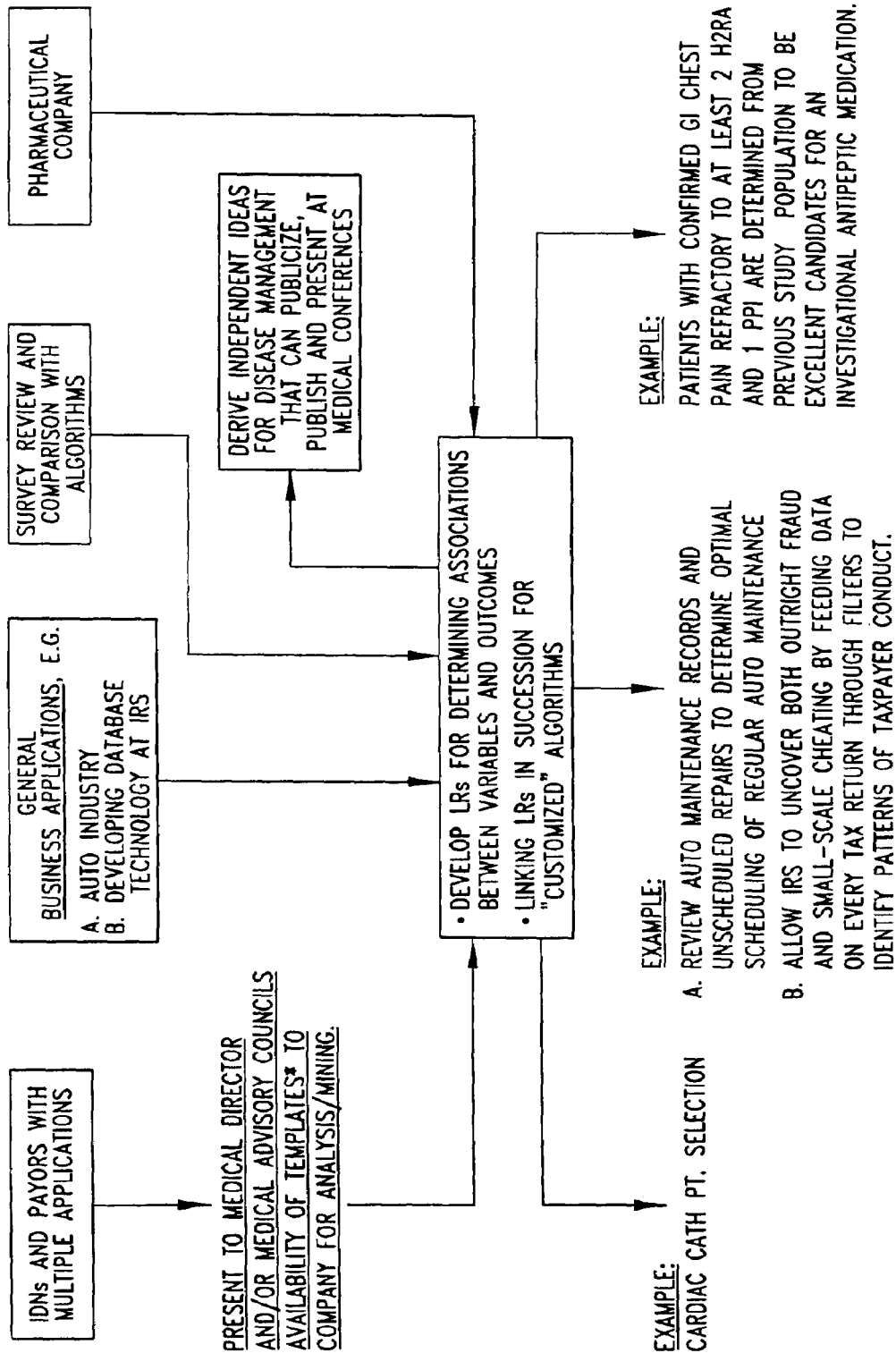
FIG. 7 shows a template algorithm for business to business.
Figure 8:
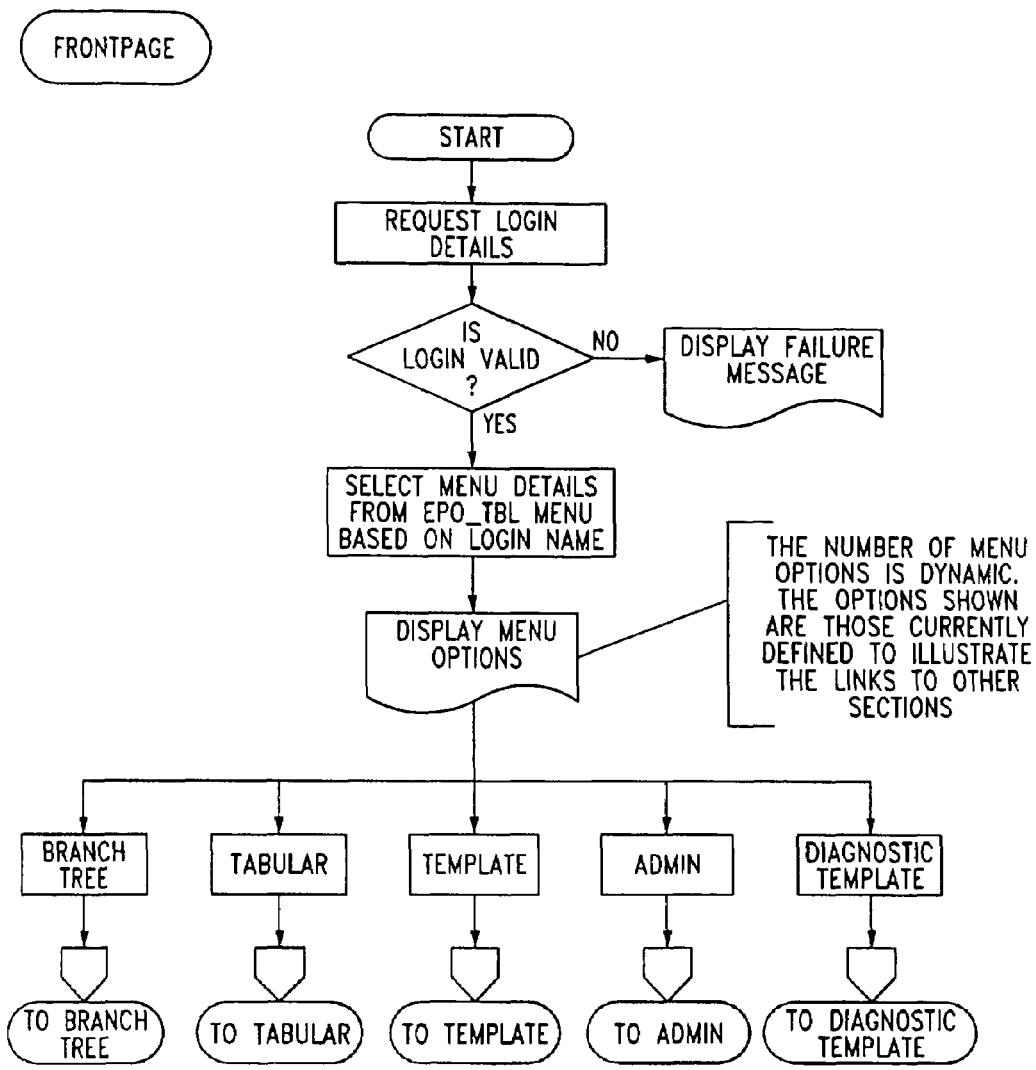
FIG. 8 shows a flow chart of the front page of a web site utilizing the method of the present invention.
Figure 9:
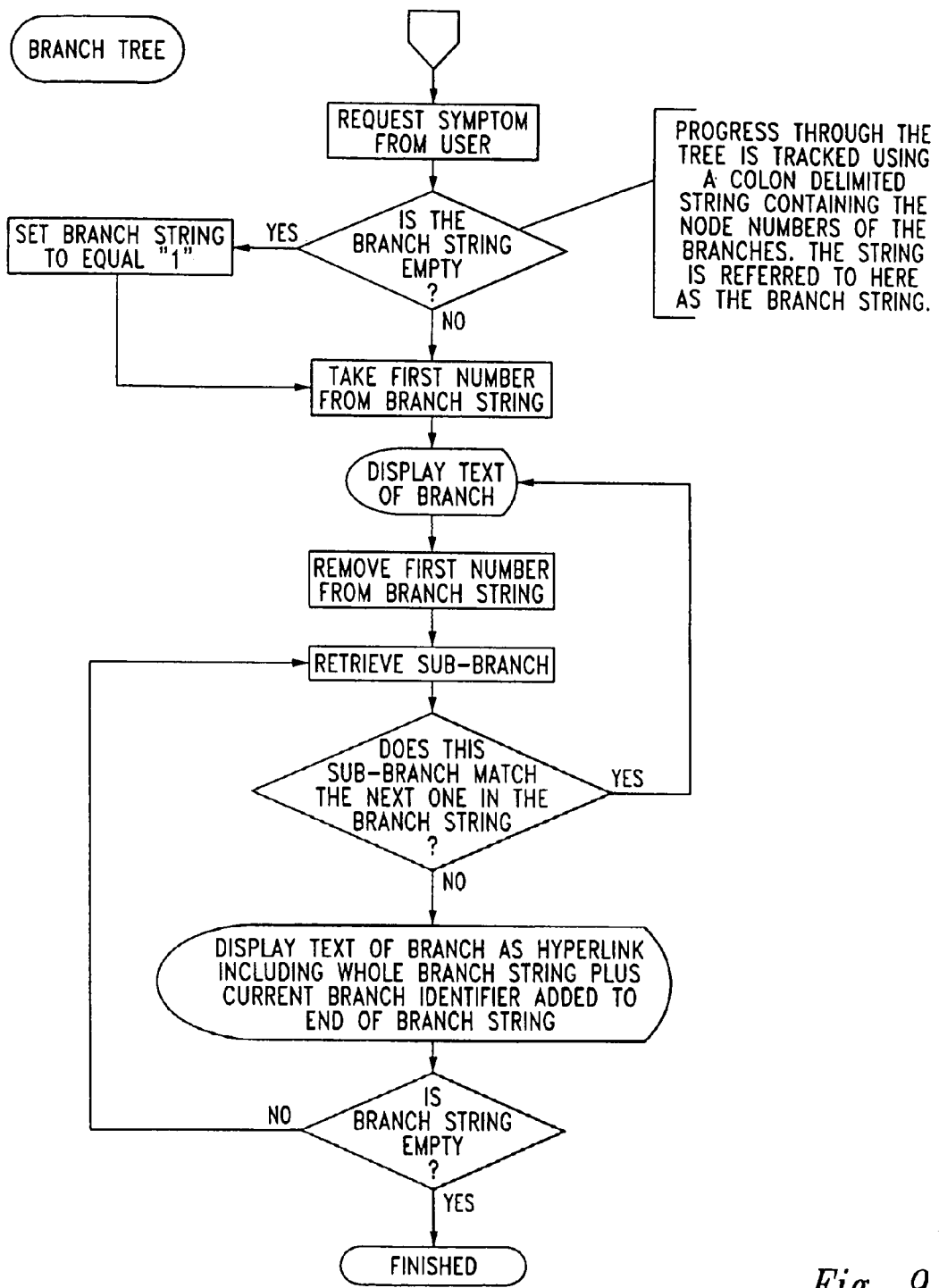
FIG. 9 shows a flow chart of the heuristics underlying a web page of a branch tree.
Figure 10:
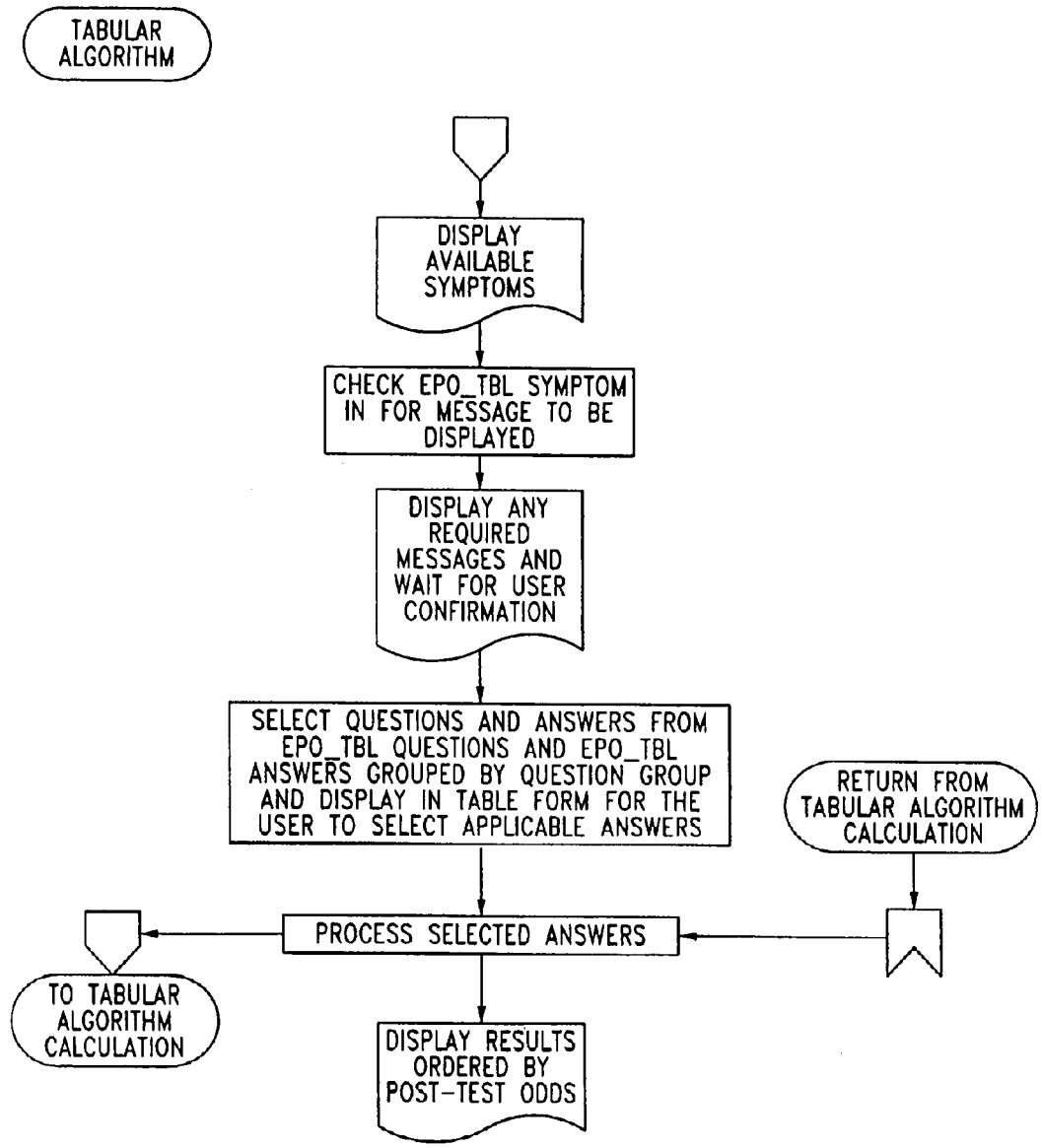
FIG. 10 shows a flow chart of the heuristics underlying a web page of a tabular algorithm

The likelihood ratios and process described herein has applicability beyond medical diagnosis. As shown in FIG. 7, for example, but not limited to, the likelihood ratios and process described herein can be used to determine likely donor suitability by philanthropic organizations and other general business applications like determination of possible audit by the IRS. In the embodiment to determine likelihood of contribution to philanthropic organizations, individuals who are likely to contribute can be identified by certain attributes. These attributes may include, but are not limited to, where the individuals live as determined by their postal code, organization of which they are members, their income, their professions, and the schools attended by their children. These, and others, are attributes that may be requested in the likelihood ratios. From these attributes, a likelihood ratio table is constructed as follows:

TABLE 7

|  | ZIP CODES | | | | |
|---|---|---|---|---|---|
|  | 33756 | 33767 | 33761 | 33752 | α |
| Donate |  | x |  |  |  |
| Do not Donate |  |  |  |  |  |
| Totals |  | β |  |  | μ |

From the above table, the likelihood ratio can be calculated as follows for a particular zip code:

LR (zip code)=$x/\alpha/\beta-x/\mu-\alpha$

The above is repeated for other attributes and the significant LR are collected. The pre-test probability is determined as discussed above. From this, the equation for probability of contribution is assembled using the following:

Pre-test odds×$LR$×$LR_2$×$LR_3$ . . . =post-tests odds

Post test odds/1+odds=probability of contribution

A certain probability can be chosen and those individuals which result above the threshold should be contacted first.

Figure 6:
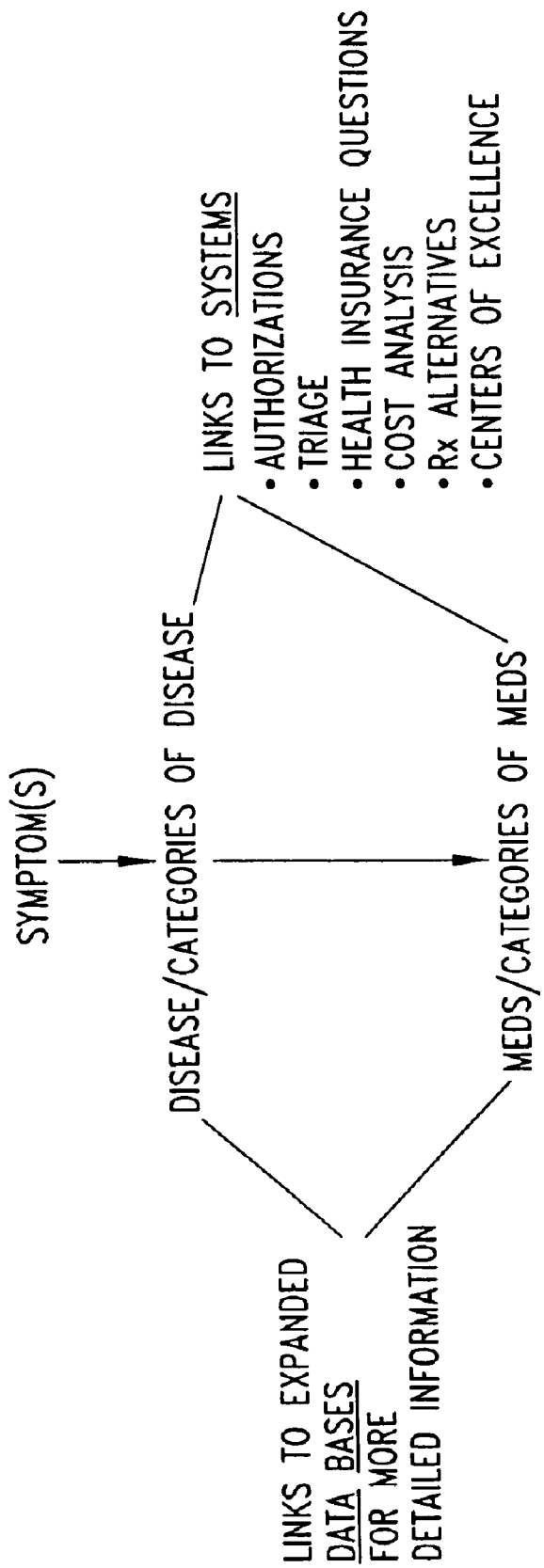
FIG. 6 shows a simple schematic of how a symptom-based algorithm is designed.

FIG. 6 provides a basic schematic flow chart showing a data processing methodology and structure according to the inventive process. Each algorithm is constructed by evaluating several variables, quantifying and combining these data, based upon probability theory to generate diagnostic alternatives. The independent probabilities involved in each branchpoint or decision step are constructed from references in the medical literature and supplanted by practices of experienced clinicians. The process for constructing such decision points and arriving at probabilities involves either a detailed search of medical literature references for actual sensitivities or specificities to determine probabilities (using meta-analysis studies) or use criteria where the potential for one choice over another is done with regard to a certain diagnosis is overwhelming. In other words, there are clinical scenarios that are so intuitive that evidence-based medicine has seen no reason to study them statistically, such as right upper quadrant abdominal pain and an abnormal liver function blood test indicating hepatic of biliary tract disease. In the situation where there is a lack of available published data but there is a clinical significance of one choice versus another choice, an arbitrary preference can be assigned to each of the two choices based upon clinical experience. Even if the actual probability, if it were to be studied, would be different, such experienced based values based upon office practice data can support uses in the inventive algorithms. Most assigned probabilities, however, will be evidence based.

The probability value is higher for an alternative closer to an "ideal solution" described in a branchtree algorithm, wherein all symptoms and branchpoint choices perfectly match the description of the user/patient, and lower for others such that it can be used to evaluate and order alternatives.

The following example looks to begin with a single symptom chest pain, and examine the various alternatives and probabilities. This will follow a hypothetical user/patient to an inventive website using the inventive process seeking to learn more about his or her own condition, manifest only as chest pain. Given that the chest pain is identified as an emergency, and there are possible cardiac etiologies, the patient/user is advised to go immediately to the emergency room (ER). In one scenario, the patient/user is evaluated in the ER and deemed to be non-cardiac, and sent home with a prescription for an H2 blocker, Zantac®. The patient/user will be told that he or she has "a bad case of indigestion" and the rest of the algorithm will follow along non-cardiac branches. The patient/user will return to the algorithm as he or she was likely unsatisfied with the unceremonious treatment or care he or she received as well as an ER charge, and will reach a branch point ultimately leading to a diagnosis of "gastroesophageal reflux disease." The reaching of the diagnosis will provide links to learn more about this disease, including a database of available treatments and alternative medications available for more informed choices. The linking databases can further discuss medical versus surgical alternative treatments for such reflux disease and other options that may exist and the likelihood of managed care providers paying for such treatments.

The "trip down the algorithm" is printable and available to transmit electronically to ones heath care provider. This allows the exercise to provide valuable information to the health care provider in taking a history for a new patient or for the symptoms presenting. The information presented substantiates the need for an appropriate level of care sought from third party payors, provides authorization for needed testing (e.g., UGI series and eventual endoscopy) and can streamline office practices. Other linking options include information for user/patient decision making, including an evaluation of different regional centers in success rates of laparoscopic nisssen fundoplication and state-of-the-art surgery for refractory gastroesophageal reflux disease. There may also be a review article link to an article describing an association between longstanding heartburn and esophageal cancer to raise a level of concern to obtain treatment. There can be links to pharmaceutical company product websites to discuss medication alternatives to the Zantac prescription and to specific online and brick-and-mortar pharmacies to advertise competing prices for a particular medication. In summary, a "chest pain symptom" can lead to potential treatment and a starting point for on-line health care information based upon diagnoses achieved by seeking proper care in a potentially emergency situation.

Chest Pain Embodiment

In one embodiment of the present invention, illustrated in the decision trees of FIGS. 2–5, a chest pain symptom is diagrammed. In the case of chest pain being a symptom of a potentially urgent disease (myocardial infarction), will have an advisory posted before the consumer is led through the decision tree of FIGS. 2–5. One example of such an advisory is as follows:

Please be advised

1. Any unexplained chest pain, particularly though not exclusively in an individual with certain risk factors, must be considered as potentially cardiac until proven otherwise.
2. Any acute or sudden chest pain requires urgent evaluation in an appropriate setting, such as an emergency room of a hospital.
3. Chest pain, though atypical in its description, still indicates cardiac disease category.
4. Although a cardiac disease may be ruled out, there are other potentially life-threatening causes that require immediate consideration for a person who is acutely (suddenly) ill. Thus a user/patient following the exemplary algorithm of "chest pain" should follow the above-noted concepts and act accordingly, particularly at asterisks and in boxes.
5. Though certain diseases have characteristics that are classically associated with them, such characteristics are occasionally absent. Therefore, one may benefit from following adjacent algorithms as well as the one that strictly follows the user's/patient's own individual symptoms. There will be language advising that if a user/patient needs to follow two or more diverging pathways because of an inability to make a decision at a decision-based branchpoint, one should follow a potentially more serious pathway first. (cardiac, pulmonary).
6. Substernal chest pain that is sharp and stabbing, rather than deep, is less likely to be cardiac in etiology (though possible).

In FIGS. 2–5, a detailed decision tree is provided that has places for additional considerations of disease categories based on patient history and for medications wherein the symptom may be the result of a medication side effect rather than an underlying disease, or the side effect is causing an underlying disease.

Within FIGS. 2–5, a substernal deep pressure precordial pain, or cardiac-type pain, is described as a pain across anterior thorax that is generally with maximal intensity in the xiphoid region. The pain is deep, squeezing, tightness or pressure. The pain is poorly localized and radiates to the neck and arms. Due to interconnecting nerve pathways involving various organs, the location of pain is this area indicates a source somewhere within the chest and upper abdomen. There are also risk factors for a heart attack to consider. These include high blood pressure, diabetes, high cholesterol, previous heart attack or heart disease and a family history of heart disease.

I claim:

1. A web-based system for facilitating diagnosis of medical symptoms comprising:
   (a) means for generating an automated database that is a real-time, web-based database that includes statistically accrued data input from multiple sources via a common web-based system template, the common web-based system template providing a medium for entering data into the database that includes actual diagnoses and patient symptoms and information from patient populations, and further, the common web-based system template being used to generate a matrix that includes a plurality of possible post-test diagnostic outcomes, each outcome indicating a possible disease and probability for the disease, and further, reporting the possible post-test outcomes to a user as a list of diagnostic probabilities ranked from the most likely to the least likely of possible diagnoses for a patient under examination; and further including
   (b) means for generating each possible post-test outcome in the matrix as an array of mathematical factors, multiplied together in series, that are based on patient symptoms and information, with one of the factors being a pre-test odds factor, and with the other factors in the array being input as a plurality of independent likelihood ratios that are produced from answers to individual patient questions and results from diagnostic tests for that patient, and wherein the likelihood ratios in the array are multiplied together with the pre-test odds factor to produce the possible post-test diagnostic outcome that indicates a possible disease and probability for the disease; and still further including;

(c) means for calculating each likelihood ratio from a web-based likelihood ratio template, the likelihood ratio template having a plurality of cells, each with an independent cell value, created by a user-selected number of rows and columns that is greater than 2×2, for calculating likelihood ratios based on more than two criteria, the more than two criteria including positive and negative test results and further including other criteria that are independent of test results, and still further, each likelihood ratio being calculated by calculating a positive likelihood ratio ("positive LR") and negative likelihood ratio ("negative LR") for each cell value in each column and each row, using an algorithm that includes the following mathematical expressions:

(1) Positive $LR=(X/a)/((b-X)/(M-a))$;

(2) Negative $LR=(a-X/a)/((M-a)-(b-X)/(M-a))$;

and wherein
  $X$=a mathematical cell value;
  $M$=the sum of all cell values across all rows and columns;
  $b$=total of specific column containing X;
  $a$=total of specific row containing X;
and still further including
(d) means for using calculated likelihood ratios from the above mathematical expressions to create the array of likelihood ratios that are multiplied together with the pre-test odds factor to create the possible post-test outcome that indicates a possible disease and probability for the disease, according to the following mathematical expression:

(3) Pre-test odds×$LR_1$×$LR_2$×$LR_3$×$LR_4$ . . . × $LR_n$=Post-test odds, wherein $LR_{1-n}$=positive and negative likelihood ratios calculated according to equations (1) and (2) above.

* * * * *